United States Patent [19]

Hergenroeder

[11] Patent Number: 4,968,316
[45] Date of Patent: Nov. 6, 1990

[54] ARTHROSCOPIC ANKLE JOINT DISTRACTION METHOD

[76] Inventor: Patrick T. Hergenroeder, 34 W. Washington St., Chagrin Falls, Ohio 44022

[21] Appl. No.: 282,589

[22] Filed: Dec. 12, 1988

[51] Int. Cl.⁵ .............................................. A61B 17/60
[52] U.S. Cl. ........................................ 606/90; 606/57; 606/58
[58] Field of Search ............ 128/92 Z, 92 ZZ, 92 ZY, 128/92 ZW; 606/90, 57, 58

[56] References Cited

U.S. PATENT DOCUMENTS

| | | | |
|---|---|---|---|
| 1,997,466 | 4/1935 | Longfellow | 128/92 ZZ |
| 2,238,869 | 4/1941 | Haynes | 128/92 ZZ |
| 3,547,113 | 12/1970 | Swanson | 128/92 ZY X |
| 3,976,061 | 8/1976 | Volkov et al. | 128/92 ZZ X |
| 4,220,146 | 9/1980 | Cloutier | 128/92 ZZ X |
| 4,554,915 | 11/1985 | Brumfield | 606/54 |
| 4,573,459 | 3/1986 | Litton | 128/92 ZW X |
| 4,628,919 | 12/1986 | Clyburn | 128/92 ZZ X |
| 4,768,524 | 9/1988 | Hardy | 128/92 Z |

FOREIGN PATENT DOCUMENTS

| | | | |
|---|---|---|---|
| 2203787 | 9/1972 | Fed. Rep. of Germany | 128/92 ZZ |
| 2601938 | 7/1977 | Fed. Rep. of Germany | 128/92 ZZ |
| 387700 | 9/1973 | U.S.S.R. | 128/92 ZZ |
| 263073 | 5/1976 | U.S.S.R. | 128/92 Z |
| 2040168 | 8/1980 | United Kingdom | 128/92 Z |
| 2126094 | 3/1984 | United Kingdom | 128/92 ZZ |

OTHER PUBLICATIONS

Chas. F. Thackray Ltd., advertisement for a Charnley Screw Jack. date unknown.
"Ankle Arthroscopy, Pathology and Surgical Techniques", by James F. Guhl M.D., copyright 1988 by Slack Incorporated, 6900 Grove Road, Thorofare, N.J. 08086; esp. pp. 46, 52, 55 and page containing FIGS. 12-1 and 12-2.

Primary Examiner—Robert A. Hafer
Assistant Examiner—Kevin G. Rooney
Attorney, Agent, or Firm—Watts, Hoffmann Fisher & Heinke

[57] ABSTRACT

An ankle joint distractor and method for spreading an ankle joint in preparation for arthroscopic surgery. The distractor comprises a pair of external fixation pins for transfixing bones adjacent the ankle joint so as to pass parallel to one another and directly through the bones from the medial side to the lateral side, and a pair of jack screws for attachment to the parallelly transfixed pins, the jackscrews being adapted to force the pins apart or together so as to distract or to compress the ankle joint while the pins are maintained in a generally parallel spaced apart relationship.

2 Claims, 3 Drawing Sheets

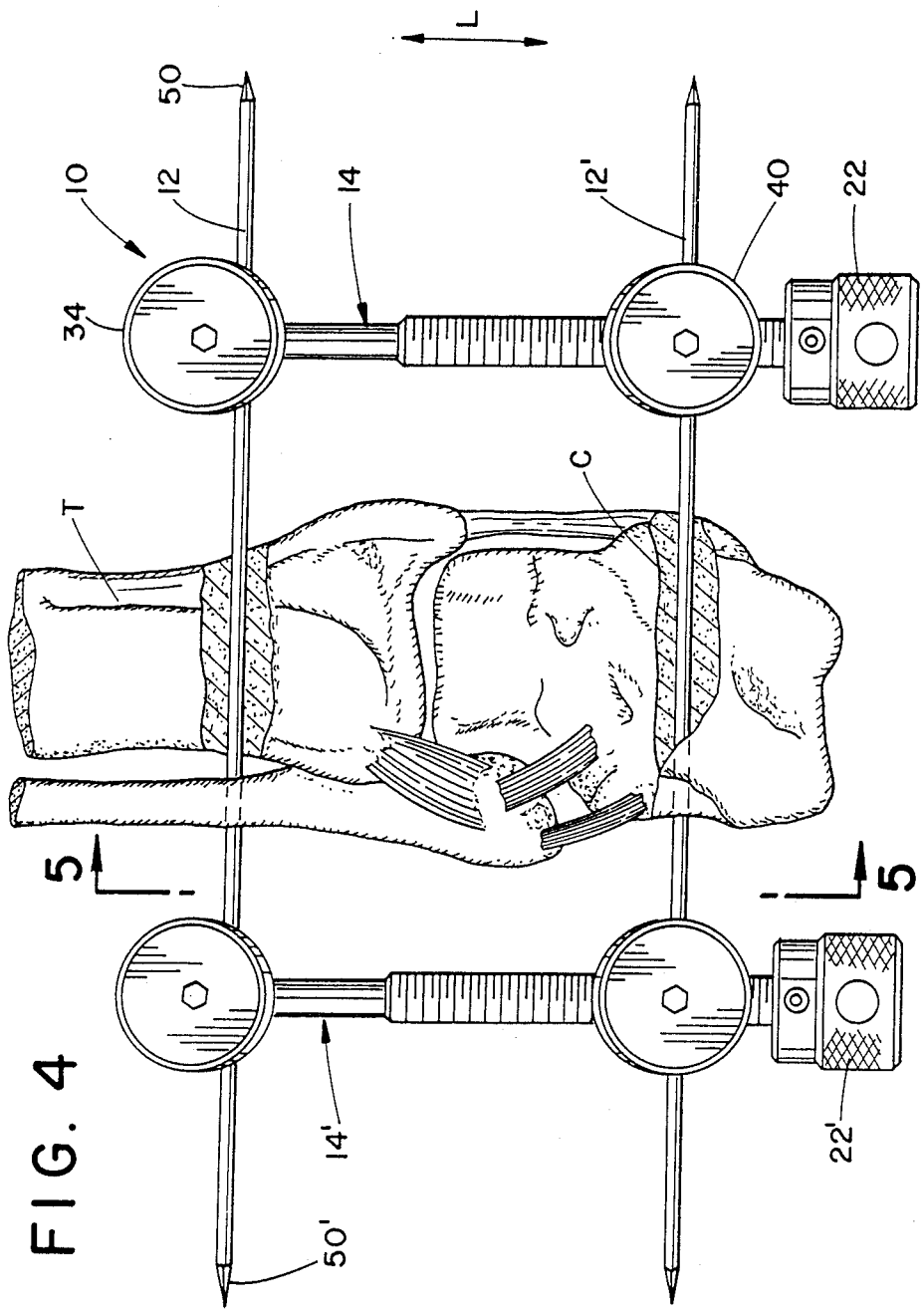

ARTHROSCOPIC ANKLE JOINT DISTRACTION METHOD

TECHNICAL FIELD

This invention relates to joint distracting and, more particularly, to an arthroscopic ankle joint distractor apparatus and to a method of distracting an ankle joint for arthroscopic procedures.

BACKGROUND OF THE INVENTION

Arthroscopic surgery includes the carrying out of various procedures involving joints, such as the knee, the wrist, or the ankle joint. During these procedures, it is necessary to separate or to distract the joint so that access to articular surfaces may be had. Access to the articular surfaces is required both to visualize the procedure through an arthroscope and to carry out procedures such as, for example, debriding. Distraction of a joint creates a space between adjacent articulated bone surfaces. Distraction of the ankle joint, in particular, creates a space between the tibia and the talus, and also the talus and calcaneus.

In the past, one method of ankle joint distraction was accomplished by placing a pair of threaded external fixation pins into the tibia and the talus. The fixation pins were placed by being driven medially or laterally into, but not completely through, the bones. The fixation pins were forced apart by a jack screw, the pins being retained in opposite ends of the screw. The forcing apart of the fixation pins distracted the tibial-talar joint from the medial or lateral side of the ankle.

In this method of distraction, the external fixation pins were placed parallel to one another (perpendicular to the axis of the leg). Forcing apart of the pins by the jack screw caused the pins to deviate from the parallel by pivoting to form an angle.

Another method of ankle joint distraction was similar to that just described, but with the difference that the distal external fixation pin was not placed parallel to the proximal pin, but at a downwardly inclining angle. Forcing the pins apart with a jack screw eventually resulted in the pins becoming parallel when the joint was distracted.

Both of these techniques suffer from the disadvantage that the distraction is performed from one side only, in this case, the medial or lateral side. Performing the distraction from one side does not create a uniform gap between the articulated surfaces. The one-sided procedure causes the bones to pivot somewhat with the result that the spacing on the opposite side will be quite small compared to that on the distracted side. This means that the flow of arthroscopic cleansing fluid will be restricted on the lateral side resulting in less effective flushing of debris and bacteria, and less access to the overall joint.

Both of these techniques suffer from the further disadvantage that the external fixation pins pass through the cortex and end in the cancellous part of the bone. When pressure is applied to the pins, the pins in turn apply pressure only to one thickness of the cortex and therefore tend to pivot and crush the soft and spongy cancellous. In attempts to alleviate the application of excessive pressure with concomitant cancellous damage, and to avoid pin breakage, various springs and strain gauges have been employed with the jack screws.

It would be advantageous therefore to provide an arthroscopic ankle joint distractor and a method of distracting an ankle joint that obviates the problems associated with prior art distractors and methods of spreading ankle joints employing these distractors.

DISCLOSURE OF THE INVENTION

The invention provides an ankle joint distractor for spreading an ankle joint in preparation for arthroscopic surgery and maintaining the distraction during surgery. The distractor comprises a pair of external fixation pins for transfixing bones adjacent the ankle joint so as to pass parallel to one another and directly through the bones from the medial side to the lateral side, and a pair of jack screws for attachment to the parallelly transfixed pins, the jackscrews being adapted to force the pins apart or together so as to distract or to compress the ankle joint while the pins are maintained in a generally parallel spaced apart relationship.

As used in the specification and the claims, the terms "transfix" or "transfixation" refer to the passage of a fixation pin directly through a bone from medial to lateral side, or vice versa, so that opposite ends of the pin stick out from opposite sides of the bone.

The term "axial" or "longitudinal" when used in connection with the apparatus or method of the invention refers to a symmetrical joint separation achieved by pulling apart the ankle joint along the long axis of the leg.

Accordingly, the invention provides an apparatus for longitudinally distracting or compressing bones at a joint comprising first fixation means for transfixing a first bone on one side of a joint relative to a direction of distraction or compression, second fixation means for transfixing a second bone on the other side of a joint relative to the direction of distraction or compression, mechanical connection means for connecting the first and second fixation means on opposite lateral sides of a joint, and distraction or compression force exerting means for exerting a force on the first and second fixation means in the direction of distraction or compression to increase or decrease a space between the bones.

The invention also provides a method of distracting an ankle joint comprising the steps of transfixing bones on either side of an ankle joint and thereafter axially separating the bones to distract the joint. The step of transfixing the bones is carried out by driving a proximal pin through the tibia, and a distal pin through the calcaneus, both transfixions proceeding medially to laterally. A two-headed jack screw is attached to the pins, one jack screw on either side of the ankle, and one pin in either head of the jack screw. The heads of the jack screws are adapted to hold the pins in such a manner that the pins may be either forced apart or forced together, depending upon the direction in which the jack screws are turned; thus, the ankle joint distractor of the present invention can be used both for distraction of the joint during the procedure and for compression of the joint after the procedure is complete. The flexible nature of the pins allows the operator to sense or visually detect flexion or bending in the pins when distraction is complete.

Accordingly, there is provided a method of longitudinally distracting or compressing bones at a joint comprising the steps of transfixing a first fixation pin through a first bone on one side of a joint relative to a direction of distraction or compression, transfixing a second fixation pin through a second bone on the other side of a joint relative to the direction of distraction or compression, mechanically connecting the pins on opposite lateral sides of a joint, exerting a distracting or compressing force on the pins in the direction of distraction or compression to increase or decrease a space between the bones, and retaining the bones in a distracted or compressed position while performing a surgical procedure on a joint.

The ankle joint distractor of the present invention offers the advantage that the joint is symmetrically and evenly separated due to the bones being pulled apart axially, that is, along the axis of the leg, rather than pried apart from either side. The equal separation on both sides of the ankle joint provides access to more of the articulated surfaces of the tibia, fibula, and the talus than was possible with prior apparatus and methods. The greater access not only facilitates the carrying out of surgical procedures, but also ensures that all surfaces will be adequately flushed with arthroscopic solution.

Additionally, employment of the ankle joint distractor allows movement of the foot in plantar and dorsiflexion during procedures. The ability to move the foot during procedures is important because it allows the surgeon to change the size of the gap between the tibia and the talus. The ability to change gap size is due to the fact that the distal pin transfixes the calcaneus leaving the talus free to move. The upper surface of the talas is not circular, but cam-like and having a different curvature at different locations. Thus, changing the relationship between the spaced apart tibia and talus by moving the foot changes the size of the gap between the surfaces.

Another advantage provided by the ankle joint distractor is due to the new ability to separate the ankle joint along the axis of the leg and equally on both sides of the joint. This advantage is, if sufficient distraction is applied, to space apart the lateral and medial gutters between the tibia, fibula and the talus. These gutters are a favored location for the accumulation of particles. The provision of an optimum gap ensures that these particles will be flushed out.

These and other features of the invention will be better understood from the following detailed description taken in conjunction with the accompanying drawings.

BRIEF DESCRIPTION OF THE DRAWING

FIG. 4 is a perspective view of the arthroscopic ankle joint distractor applied to a right ankle.

DETAILED DESCRIPTION OF THE DRAWING

Figure 1:
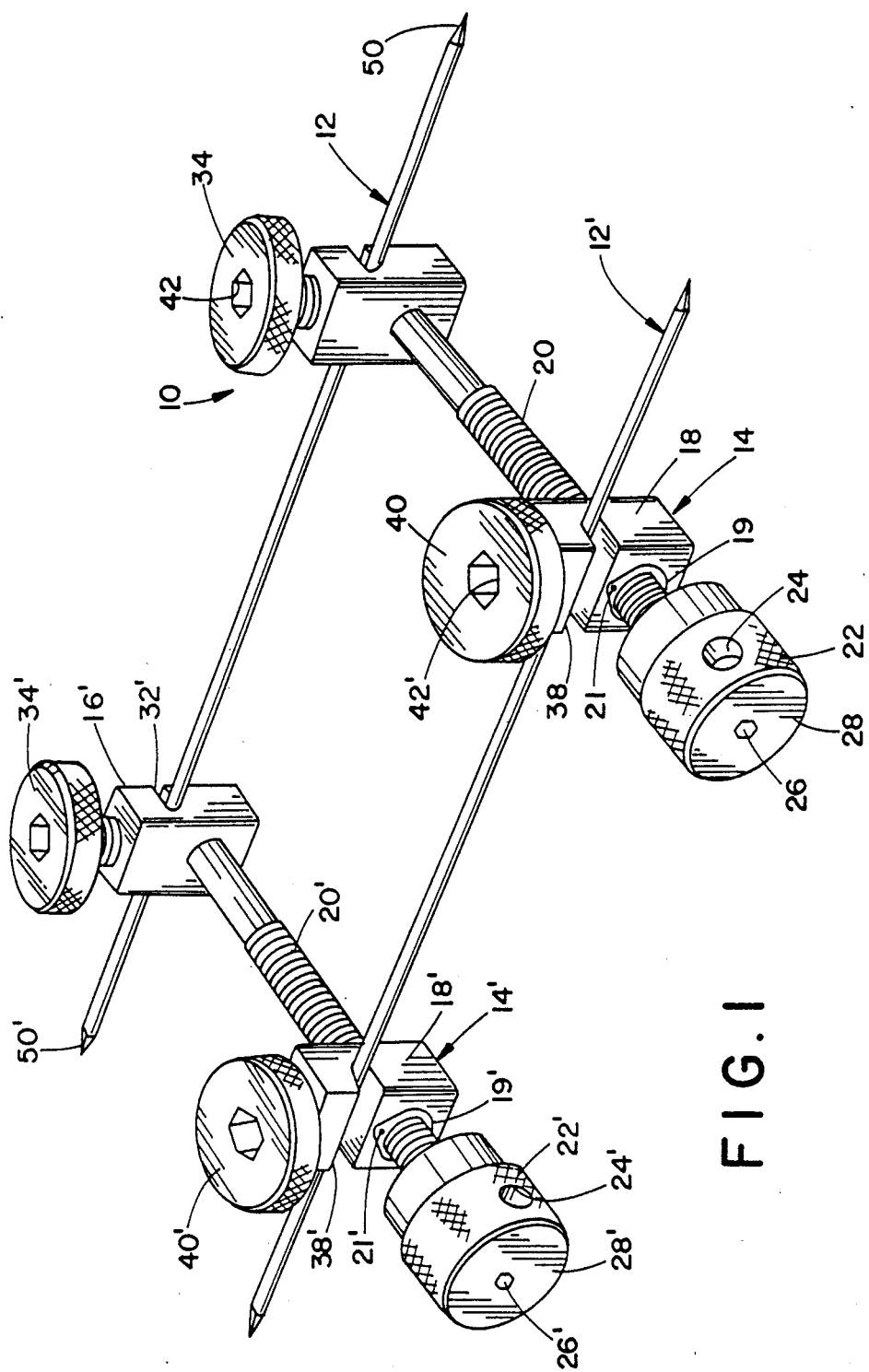
FIG. 1 is a perspective view of the arthroscopic ankle joint distractor of the invention.

Referring to FIG. 1, the arthroscopic ankle joint distractor is shown generally at 10. As shown in FIG. 1, the distractor 10 is assembled as it would be during a surgical procedure. Reference may be had to FIG. 4 for an illustration of the in vivo placement of the distractor 10. The distractor 10 comprises a pair of elongated external fixation pins 12, 12', and a pair of jack screw assemblies 14, 14'. As illustrated in FIG. 1, one external fixation pin 12 is gripped at each end in base members 16, 16' of each jack screw assembly 14, 14'; the other fixation pin 12' is gripped at each end in movable members 18, 18'. Movable members 18, 18' are provided with bronze bearing inserts 19, 19' through which the threaded jackscrews 20, 20' travel for smooth operation. The bronze bearing inserts 19, 19' are retained in the moveable members 18, 18' by means of retaining screws 21, 21'. Movable members 18,18' are driven toward or away from the base members 16,16' on the threaded jackscrews 20, 20' by means of operating knobs 22, 22'. The operating knobs 22, 22' are provided with cross-holes as at 24, 24' wherein rods, not shown, may be inserted to provide more torque in turning the operating knobs 22, 22'. Hex recesses 26,26' are provided in the ends 28,28, of the operating knobs 22,22' to allow for turning of the knobs with a screw driver having a hex end.

Figure 2:
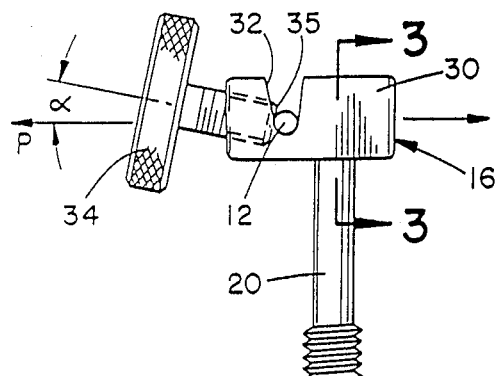
FIG. 2 is a side view of the distractor.

FIG. 2 shows the distractor from a side view. Although only those elements of the distractor visible in the side view of FIG. 2 are herein described, it will be appreciated that the following description applies equally to the elements on the other side, one side of the distractor being symmetrical with the other. As shown in FIG. 2, base member 16 comprises a first block 30 having a first pin receiving groove 32. A first finger operated set screw 34 set in the first block 30 at an angle $\alpha$ of about 10° to the perpendicular P to the screw 20 exerts a clamping force toward the bottom of the groove 32 that securely maintains and positively stops one end of pin 12 in base member 16. The first set screw 34 has a flat end 35 to engage the pin 12 in a manner known in the art. Movable member 18 comprises a second block 36 having a second pin receiving groove 38 in which one end of the pin 12' is maintained by a second set screw 40, set in the movable member 18 at an angle of about 10° to the perpendicular to the axis of the screw 20. The second set screw 40 also has a flat end to engage and to positively stop the pin 12'. The first and second grooves 32, 38 are dimensioned to just accept a pin, that is, about 7/64-⅛ inch wide. Hex recesses 42, 42', best seen in FIG. 1, are provided in set screws 34, 40 to allow for turning of the set screws with a hex nut.

Figure 3:
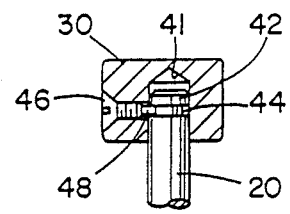
FIG. 3 is a cross-sectional view along lines 3-3 of FIG. 2.

As shown in FIG. 3, an unthreaded end 42 of the jackscrew 20 is received with a clearance fit in a blind bore 41 in the block 30. The end 42 is provided with an annular retaining groove 44. A retaining set screw 46 is threaded into the block 30 so that its retaining end 48 is received in the groove 44 with a clearance fit to allow rotation of the jack screw 20 in the bore 41 of the block 30 without allowing axial movement of the jack screw 20 within the bore 41.

Figure 5:
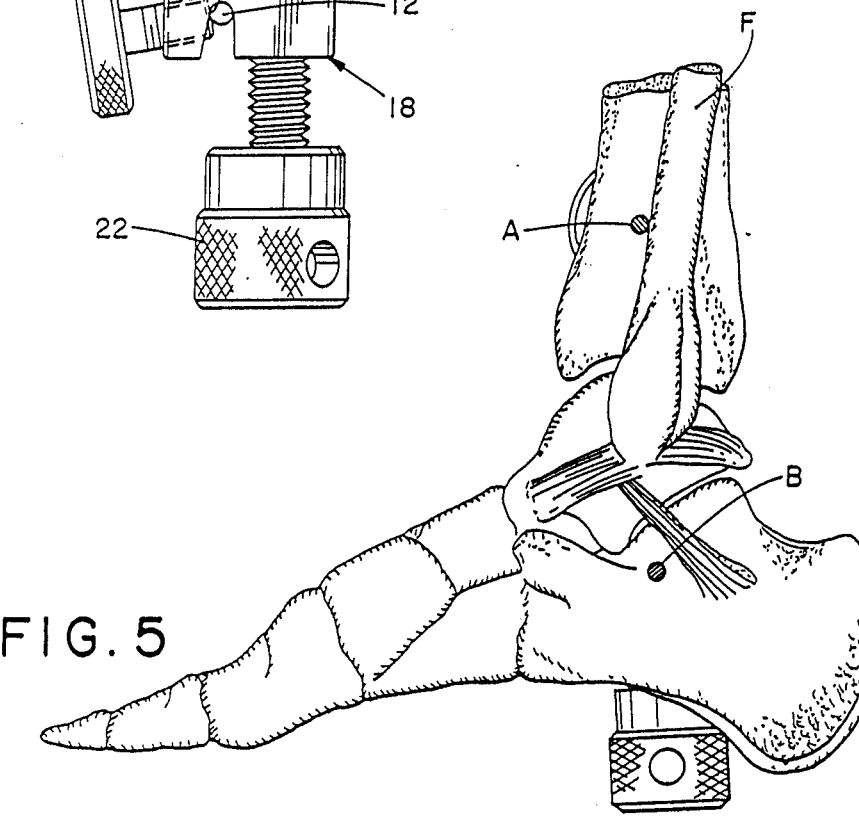
FIG. 5 is a medial view of a right ankle showing placement of the distractor pins according to the method of the invention.

The invention also provides a method for distracting an ankle joint comprising the steps of transfixing bones on either side of the ankle joint, then separating the ankle joint by moving the transfixed joints apart in a longitudinal direction. The method of distraction may be better understood with reference to FIGS. 4 and 5. FIG. 4 illustrates the arthroscopic ankle joint distractor 10 applied to a right ankle viewed from the dorsal side. Elongated external fixation pin 12 is inserted through the tibia T by means of a drill-type power tool, as is known in the art. The extreme ends 50, 50' of the have sharp ends with flat surfaces, so that the pin 12 will cut its own way through the tibia. The medial placement of pin 12 is illustrated in FIG. 5 at insertion position A. Care is to be taken to avoid insertion through the fibula F, as this bone is too fragile to support the distraction procedure. The pins are preferably about 7/64 inch in diameter and about 9 inches long. The length, however, does not matter because once the pins 12, 12' are in place and the jack screw assemblies 14, 14' attached, the ends of the pins are cut off substantially flush with the base and movable members 16, 16', 18, 18' so that the pins do not interfere with free movement by the surgeon. The pins are preferably made from chrome plated stainless steel. Most preferably, the pins are of the Steinman type (available from Richards Manufacturing Co., Memphis, Tennessee). External fixation pin 12' is driven through the calcaneus C, its medial insertion position being the sustentaculum tali, shown in FIG. 5 as position B. Once the fixation pins 12,12' have been transfixed through the tibia and the calcaneus, the jack screw assembly 14 is attached by slipping the pins 12, 12' into the oppositely facing first and second pin receiving grooves 32, 38, and then tightening the first and second set screws 34, 40. The procedure is repeated for jack screw assembly 14'. Once the ankle joint distractor is properly located as shown in FIG. 4, the operating knob 22, 22' are turned to drive the movable members 18, 18' away from the base members 16, 16' to effect distraction by pulling the joint apart in the direction L in FIG. 4. Depending upon the condition and tightness of the ligaments and tendons of an individual patient, a distraction of 6-9 millimeters is achievable. The surgeon notes when distraction is complete when deflection or bending of the pins is observed as the operating knobs are tightened. Deflection or bending signals the limit to which the ligaments and tendons can be stretched. The fact that the pins are relatively thin compared to the previously employed threaded external fixation pins is important because now spring elements or strain gauges are not needed in the jackscrews, the pins' deflection being an indicator of full distraction.

As indicated, the placement of the set screws 34, 40 at an angle of 12° allows the pins 12, 12' to be securely held within the base members 16, 16' and the movable members 18, 18' both as the movable members 18, 18', are driven away from the base members 16, 16' to distract the ankle joint and as the movable members 18, 18' are driven toward the base members 16, 16' to compress the joint. This means that after the surgeon has completed the arthroscopic procedure and has, for instance, cleaned out the joint in preparation for a fusion, the surgeon may proceed on to fuse the joint by compressing the tibia and talas together by turning the operating knobs 22, 22' so that the base and movable members 16, 16', 18, 18' move toward one another. The tibia and talas are then screwed or pinned together, as is known in the art. This ability both to distract and to compress for fusion was not available with prior art techniques and apparatus.

Variations and modifications of the invention will be apparent to those skilled in the art from the above detailed description. Therefore, it is to be understood that, within the scope of the appended claims, the invention can be practiced otherwise than as specifically shown and described.

I claim:

1. A method of longitudinally distracting or compressing bones at an ankle joint to facilitate a surgical procedure comprising the steps of:
    transfixing a first fixation pin of stainless steel having a nominal diameter of 7/64 inch through a tibia bone on one side of the ankle joint relative to a direction of distraction or compression;
    transfixing a second fixation pin of stainless steel having a nominal diameter of 7/64 inch by medial insertion through a calcaneus bone on the other side of the ankle joint relative to the direction of distraction or compression;
    mechanically connecting the pins on opposite lateral sides of the joint;
    exerting a distracting or compressing force on the pins through the mechanical connections in a direction of joint distraction or compression to increase or decrease a space between the tibia and calcaneus bones and between at least one of those bones and an intermediate talus bone;
    visually observing a definite flexure of one of said pins and thereafter applying no additional distracting or compressing force; and
    retaining the bones in a distracted or compressed position while performing a surgical procedure on the joint.

2. The method of claim 1 wherein the step of passing the second fixation pin through the calcaneus is carried out by passing the pin through the sustentaculum tali.

* * * * *